US009402748B2

(12) United States Patent
Boender

(10) Patent No.: US 9,402,748 B2
(45) Date of Patent: Aug. 2, 2016

(54) PROSTHESIS HAVING MOVEMENT LOCK

(76) Inventor: Jacob Quintus Laurens Anthony Boender, Marcham (GB)

( * ) Notice: Subject to any disclaimer, the term of this patent is extended or adjusted under 35 U.S.C. 154(b) by 0 days.

(21) Appl. No.: 13/356,560

(22) Filed: Jan. 23, 2012

(65) Prior Publication Data

US 2012/0191219 A1 Jul. 26, 2012

(51) Int. Cl.
| | | |
|---|---|---|
| *A61F 2/74* | (2006.01) | |
| *A61F 2/62* | (2006.01) | |
| *A61F 2/68* | (2006.01) | |
| *A61F 2/64* | (2006.01) | |
| *A61F 2/50* | (2006.01) | |
| *A61F 2/66* | (2006.01) | |
| *A61F 2/76* | (2006.01) | |

(52) U.S. Cl.
CPC ... *A61F 2/68* (2013.01); *A61F 2/64* (2013.01); *A61F 2/6607* (2013.01); *A61F 2002/5003* (2013.01); *A61F 2002/5006* (2013.01); *A61F 2002/5033* (2013.01); *A61F 2002/5038* (2013.01); *A61F 2002/6818* (2013.01); *A61F 2002/6854* (2013.01); *A61F 2002/745* (2013.01); *A61F 2002/748* (2013.01); *A61F 2002/7625* (2013.01); *A61F 2002/7645* (2013.01)

(58) Field of Classification Search
CPC .......................... A61F 2/68; A61F 2002/6818
USPC ................................. 623/24, 27, 39
See application file for complete search history.

(56) References Cited

U.S. PATENT DOCUMENTS

| | | | | |
|---|---|---|---|---|
| 5,376,137 A | * | 12/1994 | Shorter et al. | 623/44 |
| 5,383,939 A | | 1/1995 | James | |
| 6,106,560 A | | 8/2000 | Boender | |
| 2003/0029247 A1 | | 2/2003 | Biedermann | |
| 2005/0234562 A1 | * | 10/2005 | Okuda et al. | 623/44 |
| 2006/0155385 A1 | * | 7/2006 | Martin | 623/24 |
| 2008/0262635 A1 | * | 10/2008 | Moser et al. | 623/47 |
| 2008/0288086 A1 | * | 11/2008 | Auberger et al. | 623/27 |
| 2011/0130846 A1 | | 6/2011 | Kampas | |

FOREIGN PATENT DOCUMENTS

| | | |
|---|---|---|
| EP | 0549855 | 7/1993 |
| GB | 779087 | 7/1957 |
| GB | 2464620 | 4/2010 |

* cited by examiner

*Primary Examiner* — Jacqueline Woznicki
(74) *Attorney, Agent, or Firm* — Galvin Patent Law; Brian R. Galvin

(57) ABSTRACT

The present invention relates to artificial limbs generally and joints for same. The present invention provides hydraulic functional units whereby enabling movement of artificial joints to closely correspond with natural human movement. In the provision of realistic joints, as used in prosthetic limbs, an important aspect in achieving realistic movement is providing a different operating characteristic to the joint when under load. One important characteristic of an artificial leg for achieving a natural-looking walking gait corresponding with those of a stabilized knee, i.e. a knee resisting flexion when under load, is when it bears at least some of the weight of the amputee. Properties of resilient mechanical members are utilized to enable a hydro-mechanical system to be controlled so that it releases a low joint resistance mode relative to a default high resistance mode. The invention also permits alternative embodiments such as electronic, electro fluidic or electromechanical means.

18 Claims, 4 Drawing Sheets

PROSTHESIS HAVING MOVEMENT LOCK

CROSS-REFERENCE TO RELATED APPLICATIONS

The present invention claims priority to international application serial number GB1101097.2, with the same title, filed on Jan. 21, 2011. The disclosure of the above-referenced patent application is hereby incorporated by reference in its entirety.

FIELD OF THE INVENTION

The present invention relates to artificial limbs generally and to joints for the same. In particular, the present invention relates to hydraulic functional units, generally classified as damping devices as connected between artificial limbs whereby to enable movement of artificial joints to closely correspond with natural human movement. More particularly, the present invention relates to systems operable to reduce or eliminate inadvertent collapse of external limb prostheses, to enable movement of artificial joints to closely correspond with natural human movement.

BACKGROUND

In the provision of realistic joints, as used in prosthetic limbs, an important aspect in attempting to achieve a realistic movement is to provide a different operating characteristic to the joint when under load. Indeed, one of the more important characteristics of an artificial leg for achieving a natural-looking walking gait correspond with those of a so called (friction-) stabilised knee, i.e. a knee which resists flexion when under load, that is when it is bearing at least some of the weight of the user, for example, an amputee. As an almost default prescription item in the UK, a sudden fall or collapse in the use of an artificial limb can provide a nasty surprise. Indeed, it will be appreciated that such types of fall are a serious issue for the healthcare providers and patients alike. Other mechanical knee joints are also be liable to collapse in particular situations. Reference is made to literature associated with the Advanced Prosthetics course by J. Boender at Strathclyde University, which provides a detailed review of artificial knee joints.

Early prosthetic limb systems, dating from the 1950's were provided with friction brake devices. For example, in GB779087, when utilized in a knee joint application, there was a provided a shin and knee joint mechanism which included a drum fixed to the shin, with one or more bands connected to the thigh and embracing the drum so that the bands gripped the drum to lock the knee when the leg was bearing weight, actuating means associated with the shin and thigh operated to release the lock just before the foot left the ground in walking, with a connection between the shin and thigh permitting relative axial movement between the shin and thigh. In this device, however, an axial load on the limb produced a small rotation of the radius arm or arms causing the brake band or brake shoe to grip the drum and to resist knee flexion. Indeed, the resistance would frequently become so great such that the knee became automatically locked once sufficient load had been applied. Later devices were combined with a pneumatic piston and cylinder assembly which applied lower degrees of resistance to flexion and/or extension of the knee to control the motion of the shin during the swing phase.

In recent years, however, such friction-based systems—which required regular servicing and adjustment have been replaced by hydraulic dampers with external control, which provide resistance to flexion during a stance phase as well as a swing phase of operation by means of a piston and cylinder assembly. Hydraulic artificial knees provide stability to the prosthesis when the patient's weight is borne on the prosthesis, and collapse must be prevented. To prevent collapse of a free artificial knee joint the joint must receive appropriate information to inform it of its required mode of function. The hydraulic knee joint operates by utilising a volume of incompressible fluid to the knee joint, whereby to provide mechanical stability.

One example of such an arrangement is the hydraulic "S-N-S" knee control system manufactured by Mauch Laboratories, Inc. In some situations, however, this system required an amputee to make a knee-extending movement before flexion could be initiated. Additional problems arose through external wear and through the fact that they require actuation, which is, of course dependent upon movement being regular. As is known, when walking, one will vary one's gait to go down stairs, to cross steps, to avoid obstructions and the like. In some cases mechanical switching of the valve will not be effected properly. U.S. Pat. No. 5,376,137 to Blatchford is an example of a weight activated knee joint with hydraulic amplification of weight application triggered pivotal movement, whilst U.S. Pat. No. 6,106,560 to Ultimate Knee teaches of a weight activated knee joint with mechanical amplification of weight application triggered pivotal movement.

Whilst recent hydraulic devices are believed to be much improved they are complex and costly to manufacture; they are manufactured to high tolerances. If mechanical external valve control is provided, then there will be problems as discussed above. Alternatively, electronic control and flow control valves can be provided—that are expensive to purchase and maintain—which enable amputees to walk with a pre-determined gait yet will not necessarily be appropriately reactive to uneven surfaces.

Despite the above advances, the likelihood of buckling in an artificial knee joint in a mechanical external prosthesis remains a concern. In such devices it has proven to be possible to use the weight of the patient as a means to energise a stabilising mechanism on heel strike, whether by way of a friction brake clamp or a closure of a hydraulic valve. However, the mechanisms of such devices provide a reduced benefit when the knee joint is not extended fully upon heel strike upon a supporting surface, giving rise to a severe risk of the collapse of the transfemoral prosthesis. Examples of such prostheses are known under the following trade names: 3R80 produced by Otto Bock, Ultimate Knee produced by Ortho-Europe, Total Knee produced by Ossur. Additionally, these types of prosthesis are known from, for example, GB779087 and U.S. Pat. No. 5,376,137.

The same threshold also makes it difficult to find instant effortless stability of the knee, when extension after mid swing is incomplete the respective foot is susceptible of hitting the ground too early. This is particularly true when traversing rough, littered or overgrown pathways. Typically the weight-activation class of knee joints do not provide security against collapse in such conditions or in the event of accidental use.

To overcome this disadvantage, other devices have been made the keep the knee joint in a default state to accept weight on heel strike, and on a hyperextension of the knee joint the knee device is permitted to allow movement and release the low resistance swing mode. In this class of device, when a user faces a steep slope to walk down, an involuntary hyperextension effort is exerted on the knee joint out of necessity.

An amputated femoral end comprises a fleshy rather than boney termination to the femur, which presents problems as it sits loose in the socket with which it seeks to be securely retained. In seeking to grip with the socket or the well of the prosthesis from inside, and in preparation for movement of the hip musculature, control of the descent of the slope is enabled whilst using the 'yielding' mode of such a knee joint. Accordingly, there is a significant risk of releasing the swing mode of the prosthesis whilst expecting a yielding stance mode when collapse is imminent. An example of a presently available prosthesis which displays such a characteristic is the Mauch SNS (Ossur).

Problems arising from the use of weight activated knee joint control mechanisms include the fact that the residual weight taken by the artificial limb on toe off can be inhibitive to the release of the weight-activated mechanism. Typically an apparatus or means is supplied to cause a threshold value of weight required to activate the knee stability. This threshold is easily overcome by force acting through the heel and is not easily overcome by force acting through the toe. Nevertheless, this threshold takes away from the ease of activation on heel strike, which subtracts from the total ease of use of the artificial limb, and a minimal level of attention is required in use, although a patient will become accustomed to this and whilst the movement becomes a natural reaction in due course, it will induce an unnatural swagger, visible to onlookers and, moreover, in a lapse of concentration, when tired, for example, may cause a lapse in behaviour of the limb with a resultant fall.

An electronic solution has been found in the C-leg (Otto-Bock), wherein strain gauges are used to inform an onboard electronic algorithm about the state of the joint, such that swing release will only be permitted when a load is arising from the toe (i.e. the leg must be end of stance phase), and the knee must be straight (i.e. the leg must be end of stance phase). A load vector through the toe that does not pass anterior to the knee joint will not release the knee joint into swing. Similarly, a load that does not pass through the toe, but passes anterior the knee joint will not allow the joint to engage a swing phase mode. Whereas this solution stands out in clinical performance, these devices are too costly to be available for the common user. Moreover, it is counter intuitive to place one's body weight onto the device to secure the same body weight against sudden collapse. Thus, whilst this computerised and thus expensive prosthesis can provide a lock-out solution, since the solution is counterintuitive; when utilised it does not provide a suitable degree of comfort for the user.

OBJECT TO THE INVENTION

The present invention seeks to overcome or ameliorate at least some of the disadvantages described above. The invention also seeks to utilise the fluid properties of the working fluids and passageways to enable a purely mechanical system. Notwithstanding this, it is a further object of the invention to permit alternative embodiments such as for example electronic, electro fluidic or electromechanical means.

The present invention also seeks to provide a simple to use prosthesis which is not vulnerable to ingress of water and dirt and can be both simply and easily cleaned. Another object of the invention to provide a leg prosthesis that enables a more immediate release of a memory function, but remain sensitive to a required completion of the knee flexion movement in the first half of the swing phase, when required as is the case across uneven terrain.

STATEMENT OF INVENTION

In accordance with the present invention, there is provided a prosthesis in accordance with the features of claim 1. The present invention thus utilizes two small displacements within the construction of the joint that both provide part input into a compound displacement (to create an 'AND'-gate function) that can energise a means to alter the generic state of the joint, typically a change from high resistive torque (stance security) into low resistive torque (swing). Further the present invention may further introduce a suitable memory to maintain the output of the 'AND'-gate function to facilitate the ease of switching over from high torque to low torque, and back.

The hydraulic actuator (that provides the resistive torque in the joint) can comprise one of a rotating vane in a suitable housing assembly, a cog pump, a moveable end portion of a bellow body, in which embodiments either part can be said first means, or in which said first means is a membrane or a free piston sealing a fluid space, which said membrane or free piston converts an external hydraulic fluid pressure on the outer membrane or free piston face into a force through the body of the membrane, which said body of the membrane or free piston converts the force into the said first pressure. This actuator also includes at least one valve to control the state of the actuator. This valve is directly or indirectly controlled by the compound input, and may in the same embodiment also provide the memory function. Alternatively the switching and the memory function may be separated out.

The limb can be a leg, with the first artificial limb component being an upper leg element and the second artificial limb component being a lower leg or a hip element, the joint pivotally coupling said first and second limb being a knee or hip joint. The limb can be an arm with the first artificial limb component being an upper arm element and the second artificial component being a lower arm limb or shoulder element, the joint pivotally coupling said first and second limb being an elbow or shoulder joint.

The prostheses in accordance with the present invention can comprise one of or both an artificial skeletal limb or a brace for hip, limb or ankle. Conveniently, the valve is adjustable to provide variable conditional control to the motion of said joint by permitting changes to its angular status. The fluid can be selected from one of a combination of the following fluids; a hydrocarbon based fluid, a silicone based fluid or rheomagnetic fluid.

Thus, in one aspect of the present invention, upon a return to a natural weight accepting state of the knee joint there is no delay to a further state of movement of the joint, for example, upon the occurrence of lifting off the weight of a body upon a prosthesis, the lower part is free to swing in a controlled fashion i.e. a state permitting free knee flexion), this by drawing on the energizing and informing potential of the existing reverse pressure differentials present during the extension phase in the second half of the swing phase. Due to the relative high levels of energizing power available during knee extension and the distinct and logical onset of its availability, its use is an inherent advance in the logical control of an artificial hydraulic knee. Notwithstanding this, if further delay is required, then additional control systems could be employed, to act in an ancillary fashion. A further enhancement and alternative is the making available to a user an adjustable time delay for the memory to turn to a default state.

The present invention in one aspect thus resides in the utilization of two signals derived from the 'a single force vector' whereby the prosthetic joint can filter out force vectors that excite only a first signal as is known from, for example, a weight activated joint that would cause collapse of such a known joint) or the joint to filter out force vectors that excite only a second signal as is known from, for example, a hyperextension deactivated stability that would cause collapse of such a known joint), and by filtering out the erring force vectors only the safe ground reaction force vectors are permitted to release the joint into swing (i.e. into low torque mode).

The use of more than one signal has been used in software driven joints, wherein strain gauges and goniometers inform such software to be used in algorithms, but so at a huge financial cost to the buyer, as well as the complexity of using onboard batteries, servo motors, sensors, on board computing, calibration etc. This disclosure maintains a level of simplicity by using readily available mechanical and hydraulic means to provide an advantage not yet seen in the mechanical joints.

In another aspect of the invention, there is provided a prosthetic joint with two effective axes in its construction that can flex one or another way depending on the origin, direction and magnitude of the force vectors passing through and around the prosthetic joint, and wherein each of the said effective axes can produce a mechanical displacement against the resistance of an associated resilient member, when the said force vector favourably passes each of these said effective axes, and wherein the mechanical displacement is delimited to a maximum such that these said displacements can be evaluated as a total displacement, such that the total displacement can be evaluated to be greater than either one said mechanical displacement to be energise a means to release the prosthetic joint in a low resistance mode against flexing, and said means includes an aspect to maintain the said means in an energised state whilst the joint continues its flexural movement, even when either or both of the initial said mechanical displacements are no longer present to energise the said means.

Thus the invention utilizes the properties of resilient mechanical members to enable a hydro-mechanical system to be controlled in such a fashion that it only releases logically a low joint resistance mode relative to a default high resistance mode. The invention also permits alternative embodiments such as for example electronic, electro fluidic or electromechanical means.

BRIEF DESCRIPTION OF THE DRAWINGS

Reference shall now be made to the drawings as shown in the accompanying drawing sheets, wherein:

FIGS. 11 and 11a show the operational logic of the present invention; and,

FIG. 11b showing possible locations of sensors;

LEXICON

The following terms have specific meanings and it is intended that reference shall be made to this lexicon in event of any doubt:

Brace: a support device to maintain a relative position of a limb with respect to the trunk or another limb; part of an external frame work arrange about and intended to support limbs;

Hydraulic fluid; a substantially incompressible fluid operable in hydraulic lines, hydraulic rams and hydraulic systems;

Hydraulic damper: a hydraulic device comprising at least a first variable volume of hydraulic fluid, wherein the volume of hydraulic fluid retained within the hydraulic actuator is proportional to an amount of actuation associated with a joint to which the hydraulic damper is coupled;

Prosthesis: an artificial part such as an artificial limb; an artificial or mechanical aid such as a brace;

Prosthetic joint: an artificial joint associated with the repair or replacement of a skeletal joint; the term includes external orthopaedic joints;

Orthopaedic joint: a skeletal joint; a joint of the limbs; a joint such as the hips;

Valve: a device operable to regulate or control the flow of a fluid in a passageway, such as a pipe or duct, between two volumes; a device operable to regulate or control the flow of a fluid, but not necessarily preventing flow of said fluid.

DETAILED DESCRIPTION OF THE PREFERRED EMBODIMENTS

There will now be described, by way of example only, the best mode contemplated by the inventor for carrying out the present invention. In the following description, numerous specific details are set out in order to provide a complete understanding to the present invention. It will be apparent to those skilled in the art, that the present invention may be put into practice with variations of the specific.

Figure 1:
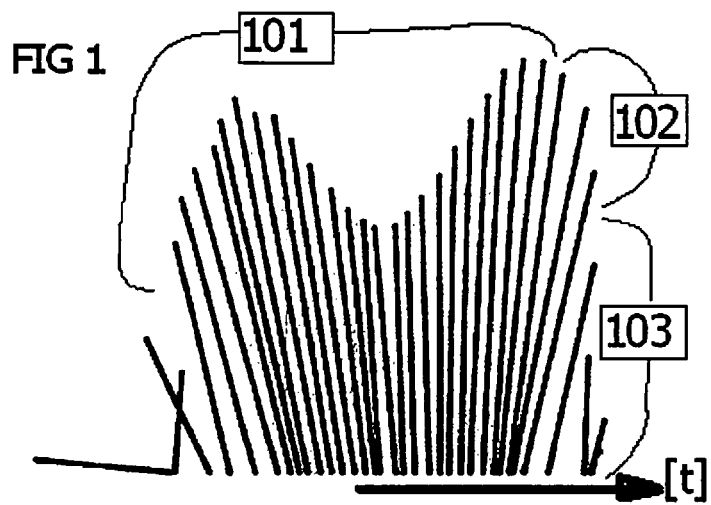
FIG. 1 shows a Butterfly Diagram typical of a gait analysis recording.

FIG. 1 shows a 'Butterfly Diagram' wherein a sequence in time of vectors are depicted with the origins of the vectors from the contact surface in the ground (the beginnings of the lines at the lower aspect of the diagram, The force vectors have a length (the magnitude of the force) and a direction (the inclination of the vector) and an origin in the walking or supporting surface. These diagrams are typically found in research in gait analysis and are indicative for normal and abnormal gait. It is important that these represent reliable and common patterns.

Figure 2:
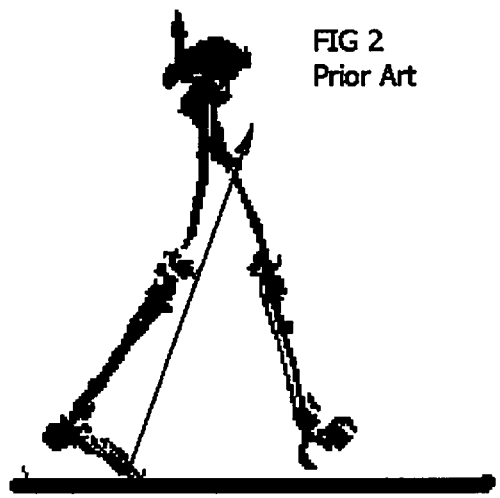
FIG. 2 shows a skeletal frame with a single vector arising from under the ball of a foot.

FIG. 2 shows a snapshot in time of a skeletal representation of a normal person walking where a single vector is shown arising from under the ball of the foot. The vector acts in front of the knee joint just prior to the knee engaging in the swing phase. Whereas a normal leg has musculature and reflex response control, an artificial knee joint has little information to ensure that the knee is stable (whilst weight bearing on it) and that the movement through the knee is supple (whilst swinging through). The knee joint must make a decision when the stability is to be engaged and when the suppleness is called for.

If the skeletal figure in FIG. 2 were to be understood to be an artificial leg, then a vector passing in front of the knee would cause the same to extend until it meets a mechanical blockage preventing further motion. If the force vector passed posterior to the knee joint, then the knee would bend and the patient would be liable to collapse.

Figure 3:
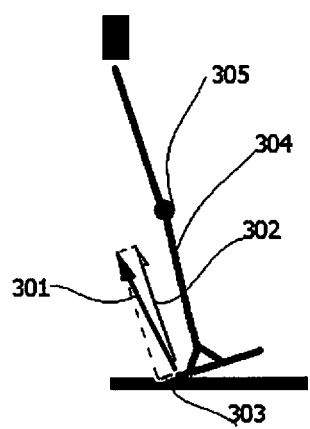
FIG. 3 shows a simplified figure corresponding to FIG. 2.

FIG. 3 shows a simplified leg corresponding to the skeletal leg of FIG. 2, although the timeframe corresponds with heel strike. Vector 301 indicates a force in heel strike that has an axial component 302 (parallel with shin 304), and a perpendicular component 303. Whereas in a weight stabilised joint, the force vector component 302 must be large enough to trigger the mechanism within knee 305, the force component 303 must be small enough to not prematurely bend the knee about 305 and induce a collapse. Whilst this mechanism works well within the normal range of force vectors in a normal butterfly diagram, the ground reaction vector in a stumble is causes 303 to be very large. In contrast, in a scuff action, for example, the reaction force 302 would be rather small. These conditions can induce a liability for the limb to collapse.

One general problem associated with mechanical joints is that the response of the joint controller is dependent upon a load applied but not necessarily in accordance with a desired kinematic requirement independent of load. This means that a correct and safely maintained response is required in each of the two alternating operating states of a prosthetic; namely, a low reactive torque state, such as typically in a swing phase, and a state of high reactive torque under the bearing of weight. An inappropriate torque level typically means a severe disruption of gait.

Figure 4:
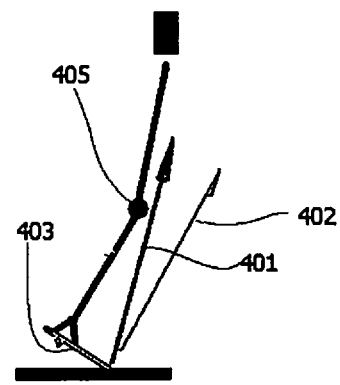
FIG. 4 shows the vector components in a pre-toe-off condition in gait.

FIG. 4 shows the vector's force components in a pre-toe-off condition in gait. Force vector 401 can be considered as a knee bending vector component 403 and a knee straightening vector component 402. As the leg is straightened, a sensor means in the knee joint 405 can detect a balancing of forces. The sensor means, conveniently a resilient member, enables a small displacement of the sensor to occur, which movement actuates a valve, conveniently with a memory function, whereby to enable release of the joint for swing.

Figure 5:
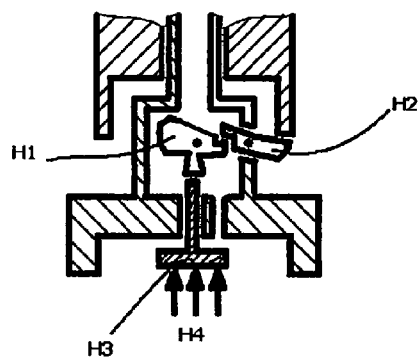
FIG. 5 shows a known mechanical switch with memory.

FIG. 5 shows an example of a prior art mechanical memory. Specifically, the memory comprises an eccentric toggle H1, that resumes a gravitational neutral position unless prevented by an open state of a valve member H3, which is energized by hydraulic pressure H4 caused by a flex movement of the free knee. It is notable that this linkage is not instantaneous; release of the memory function takes a time period independent of the time it takes to reapply weight on the prosthesis. In the event of an inadvertent early reapplication of weight on the prosthesis, the toggle would probably not be in a position to allow closure of the valve, which could be painful and perhaps cause an prosthesis user to fall following knee collapse in such circumstances. In effect, the memory of this prior teaching is continued for a longer period than desired whereby to cause at the very least a non-natural gait, with an increased likelihood of a fall occurring due to the time required for a change in state being far greater than desirable. A reflex style pushback in the leg by the amputated femur causes the swing to be released, which is good in normal swing but the leg causes to be very liable to collapse in downslope walking.

Reference is made to "Mechanisms of stumble recovery: Non-microprocessor controlled compared to microprocessor-controlled prosthetic knees" K Kaufman et al, wherein it was concluded that neither weight activated stance stability, nor knee-hyperextension deactivated stance control provided a suitable degree of safety for the user, although it was reported that one microprocessor knee was reported to provide a sufficient degree of surety.

The safety in the prior art microprocessor knee follows from a two condition input instead of the single condition inputs in the state of the art mechanical knee joints. In the microprocessor joint, the chosen inputs are firstly a determination of a ground reaction force passing in front of the knee joint axis through data collection by strain gauges in the distal part of the chassis relative to the joint, and, secondly ascertaining that the knee angle is 180° (i.e. being straight). These methods act as filters for particular conditions.

Figure 6:
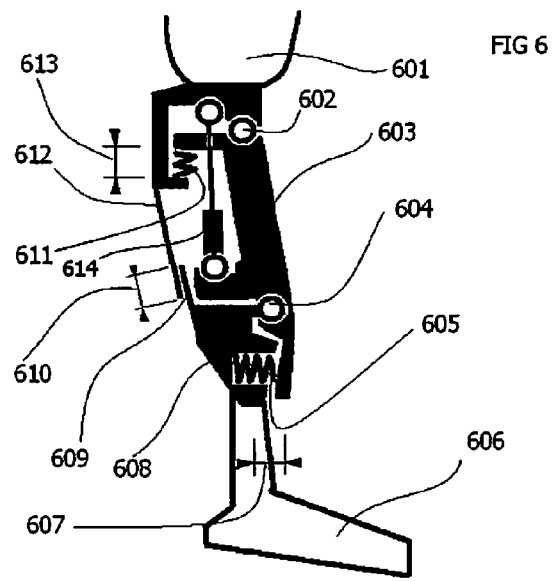
FIG. 6 shows a first embodiment of the invention.

A first embodiment of the invention is shown as in FIG. 6. In this figure, there is a stump attachment 601, a principal knee axis 602, a chassis 603, an auxiliary axis connection 604, a foot portion 606, a first resilient member 611, a second resilient member 605, a member 608 fixed to the foot portion pivotally linked to chassis 603. Thus movement by extension is resisted by resilient member 605, and the resilient member 605 allows a range of movement 607 that is input to the corresponding total displacement 610. Further input into total displacement 610 deflection of resilient member 611 when the chassis pivotally extends about pivot 602 relative to 601. By the use of suitable materials, it will be apparent to the man skilled in the art that a degree of inherent resilience of the chassis may provide a sufficient degree of resilience whereby the specific use of first and second resilient members is not necessary.

The device is manufactured such that when there is only one input signal—of two required signals, then such signal is not sufficient to enable displacement, or a signal 610 large enough to affect the state of the controller 614, that provides a resistance to a variation in its telescopic length, and which is pivotally connected to members 610 and 603. Advantageously the controller 614 reduces the resistance to compression significantly when signal 610 achieves a required minimum value. The controller may comprise further means that acts as a memory and will maintain the controller in a low resistance mode (in lieu of signal 610) until the controller extends as a result of the joint extension, which will null the memory and bring the controller in a state of readiness of providing high resistance against compression, unless signal 610 is reapplied.

In terms of gait analysis, 611 can only provide a signal 613 when the knee hyper extends, and that is only possible with a ground reaction force passing anterior to the knee joint, providing inherent stability to the knee joint. Further, again in terms of gait analysis, 605 can only provide signal 607 with a ground reaction force passing in front of pivot 604.

Figure 7:
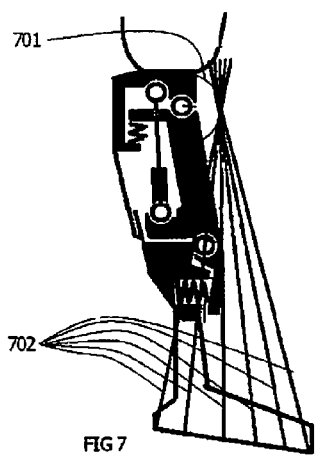
FIG. 7 shows the first embodiment indicating a radius of minimum hyperextension torque.

In order to explain the induced signal 613, reference shall be made to the first embodiment in FIG. 7, where there is indicated a distance or radius 701 representing a minimum required hyperextension torque 701 about pivot 602. There is shown a number of possible ground reaction force vectors 702 that arise from a number of possible positions that the foot can create input 613. The minimum hyperextension torque 701 acts as a filter to screen out any force that passes too close or posterior to the auxiliary knee centre 604 to effect signal 607.

Figure 8:
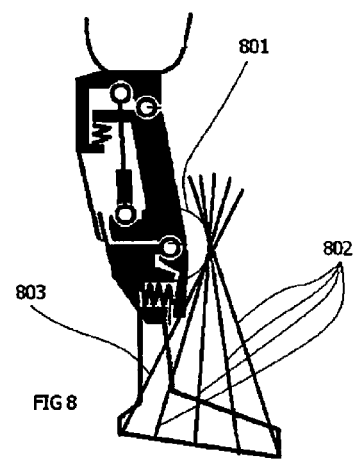
FIG. 8 shows a similar radius of minimum hyperextension torque about a pivot.

In order to detail the induced signal 607, FIG. 8 shows a similar radius of minimum hyperextension torque 801 about pivot 604. An array of force vectors 802 is indicated that would meet the direction and magnitude and origin to meet the requirement to make input 607. Vector 803 is a sample of a possible vector, but non-occurring in the normal ground reaction space envelope, or butterfly diagram. To produce a vector like 803 the heel would need to be slapped backwards onto the ground in a hammer-back-slap like action. The minimum hyperextension torque 801 acts as a filter to screen out any force that passes too close or posterior to the knee centre 602 to effect signal 613.

Figure 9:
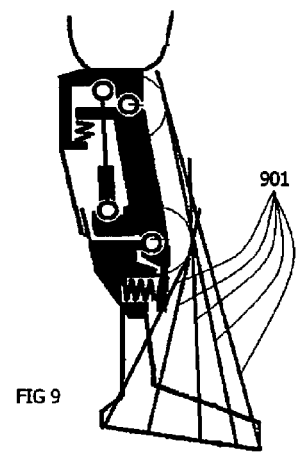
FIG. 9 indicates a number of ground reaction vectors that would meet the requirements for operation of the invention.

FIG. 9 shows a range of ground reaction vectors 901 that would meet the requirements to create compound input 610. The geometrical limitations to the signal strength of 607 and 613 make these signals digital rather than analogue, and suitable for processing through a logical port, a logical AND-gate, which in our preferred embodiment is purely hydromechanical.

When the available force vectors as illustrated in FIG. 1 are superimposed onto the knee joint it becomes apparent that only the force vectors indicated within bracket 102 are of sufficient magnitude and direction to pass both filters 701 and 801 to produce compound signal 610. It follows all realistic vectors that can create compound input 610 also naturally stabilize the knee joint against collapse. Bracket 103 in FIG. 1 indicates force vectors that are of insufficient magnitude to produce both signals/inputs 607 and 613.

The second aspect of the invention is the provision of a memory mode that can maintain the energizing power of 610 to release controller 614 into a low resistance mode, so that the ground force vector can be directed in a posterior sense with respect to the knee joint axis 602 by movement of the amputation stump 601 upon hip flexure effort. For clarity, the overlapping of the parallel members that form 601 only serve to indicate that movement, and show a possibility of displacement measure, and does not form the representation of an actual construction. In fact 601 could represent be a closing gap (suitable for electrical contact making), an overlap (suitable for a variable resistance contact making), a resilient member (suitable for strain gauging), or a means to open a hydraulic valve to permit a hydraulic flow.

FIG. 6 is shown as one of a large number of types of possible construction of prosthetic. Since connection 604 allows only a minor degree of pivot action, it can be provided as a resilient member, a hinge or otherwise, provided that a signal at 610 can be determined. It is also possible that an element with a known resilience so as to combine the properties of elements 604 and 605 could be provided so as to enable the provision of a contribution to the compound signal 610.

Signal 610 could also be embodied within damping control means 614 when the signal 607 (arising from a pivotal motion) contained in member 609 is passed to the damping control means 614, and when signal 613 is passed through into controller 614 when member 1006 is part of the piston rod of controller 614. In this way the signals are preserved, but neatly brought into the centre of the controller for hydraulic processing.

Electrical switches could be activated to determine a digital switching mechanism: a variable resistor could be arranged to provide an analogue state—in either of these alternatives, an electronic capacitor could be permitted to gain charge, and on maintenance of that charge the controller 614 could be made free by maintaining a solenoid valve state. Equally mechanical memory the same as or similar to FIG. 5 could be employed.

Figure 10:
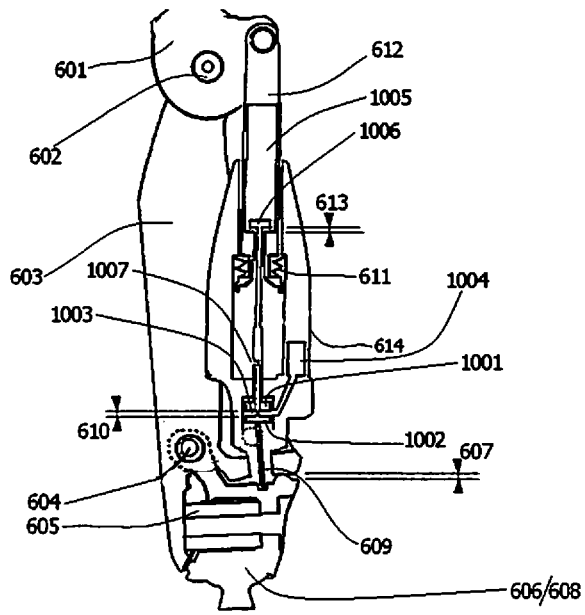
FIG. 10 shows a second embodiment of the present invention.

The second embodiment as shown in FIG. 10, comprises a hydraulic solution wherein a valve 1001/1002 is disposed in controller 614 which valve, in an open state, permits a low resistance state of the controller. The reference numerals of his Figure correspond with those of FIGS. 6-9. Two valve bodies are constructed such that the valve is closed when these bodies meet and the valve is open if the valve bodies are parted. The valve is constructed such that with a minimum input 613 the top valve body is raised, and with a minimum of input 607 the lower valve body is drawn down. Due to the fact that valve body 1001 can be raised up by member 612 against resistance of resilient member 611, and valve body 1002 can be pulled down by member 606/608 a gap 610 can form.

Accordingly, signal 613 is produced in such a way that member 612 can produce the signal by over extending the knee joint, but cannot remove be removed solely upon flexion of the knee joint. Head 1006 can therefore move freely in space 1005. On depression of piston 612 hydraulic fluid flow commences through passage 1007, which by virtue of pressure drop 1003 between valve members 1001 and 1002 will maintain these valve members in an open condition—and keep the valve open during knee flexion motion—although, for clarity hydraulic fluid drain paths necessary for this are not shown. This creates the required memory to permit low torque resistance to the knee joint flexion. On extension, the pressure drop 1003 is lost (due to a different return flow from accumulator 1004 by means of one way return valves, also not shown, and the valve bodies 1001 and 1002 close again preparing the joint for high torque resistance use, such as required for knee stability under the bearing of weight.

Whereas this means of providing a memory is the preferred means within this disclosure, a means such as described in FIG. 2 in GB2464620 (prior Art) would also be employable.

The present invention benefits from the use of known components that are widely employed yet arranged in a distinct fashion whereby to create a logical AND-gate, as per example made by the sufficient lifting of valve member 1001 AND sufficient depression of valve member 1002, which conditions must BOTH be TRUE to permit a flow of fluid to pass through the valve which causes a low state of resistance against bending the joint about axis 602. For the avoidance of doubt, the hydraulic fluid under piston 612 causes a pressure on valve member 1001 to enforce closure once closed.

Figure 11:
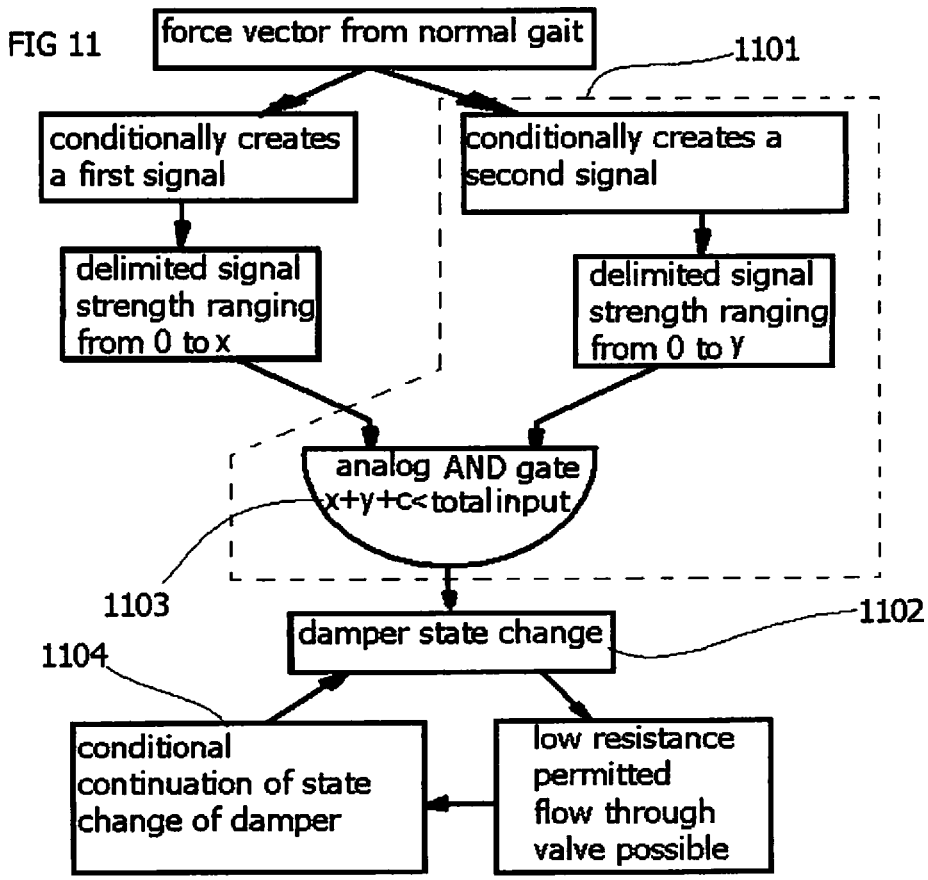
Figure 11:
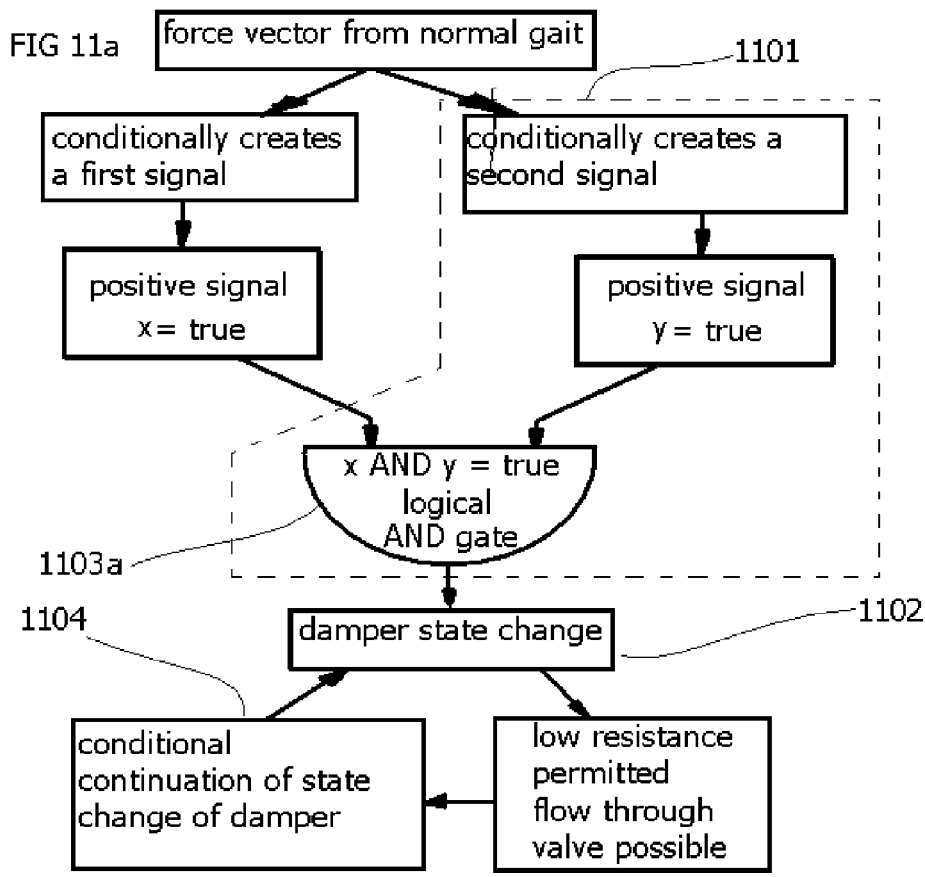
Figure 11:
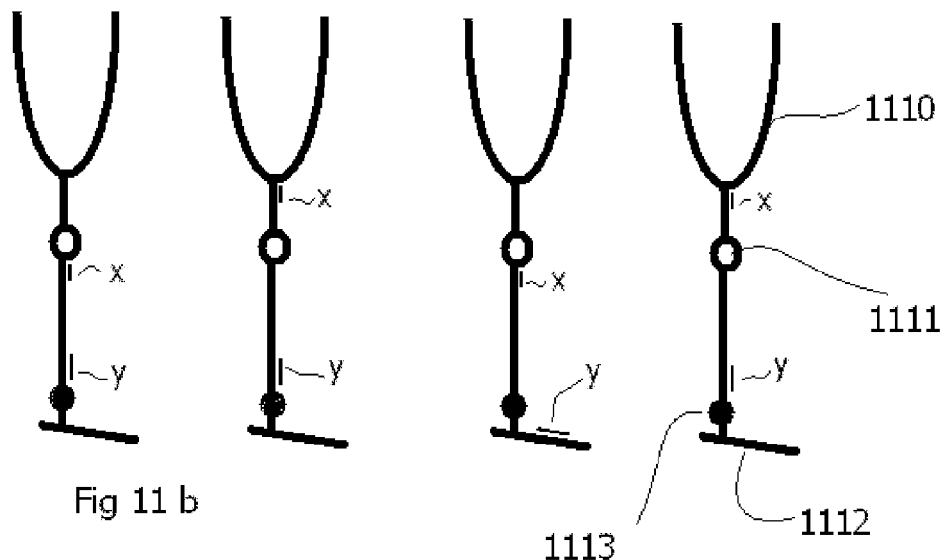

FIGS. 11 and 11a show the operational logic of the present invention. Box 1101 delimited by dashed lines, comprises the logic step comprising a second signal as a part requirement to enable a low resistance functional mode of the joint by evaluating an AND logic condition 1103 and 1103a, such that the force vectors arising from normal gait conditionally (depending on origin, direction and magnitude) create signals that need to be summed to a required value to energize a valve 1102 and associated memory 1104. This added requirement makes a distinct difference to any known mechanical joint on the market, as it removes the effects of weight bearing on the heel and hyperextension through muscular effort as a mode to release swing phase; indeed, this is a different mode to known computer controlled systems that permit swing initiation on weight bearing on the toe combined with angular measurement i.e.: 'continuously monitoring AKP knee angle' (U.S. Pat. No. 5,383,939) 'electronic sensing means for continuously monitoring position of the center of gravity of the user's body relative to the AKP foot and emitting signals representative thereof' (U.S. Pat. No. 5,383,939), of the knee being straight using 'programmed computer means for receiving the emitted signals' (U.S. Pat. No. 5,383,939). It also makes a distinct difference to the known weight activated joints, as the release of swing by weight bearing on the toe is facilitated instead of resisted as in the known weight activated joints, that need springs to overcome that problem, with the same springs resisting the efficacy of the joint stabilising with weight bearing on the heel. The present invention is further distinct to the known hyperextension release mechanisms, as such hyperextension effort alone is insufficient to permit low resistance knee flexion.

To avoid doubt, FIG. 11 shows AND gate 1103 using delimited analogue signals or inputs x and y, and in order to energise the switchover 1102 and subsequent memory 1104 it requires the total input to be greater than x+y+c, wherein c is constant to represent a margin of safety. This analogue signal processor describes the hydraulic solution as drawn in FIG. 10.

FIG. 11a shows essentially the same AND gate 1103a using logical input signals or inputs x=true and y=true, and in order to energise the switchover 1102 and subsequent memory 1104 it requires the inputs x and y both to be logically true. The logical gate is the preferred description if for instance normally open electrical switches x and y are put into a series to form an AND gate (1103a). Alternatively the signals x and y could be derived from signals from strain gauges that produce signals from two height positions within the limb prosthesis. The advantage of using strain gauges is that these can be placed in various positions in leg prosthesis as illustrated in FIG. 11b, with stump receptacle 1110, knee 1111, ankle 1114, foot 1112. The requirement in accordance to the invention is that these are located in suitable places to sense an hyperextension moment in two locations in the leg prosthesis such as to only permit force vectors anterior to knee 1111 and ankle 1113 joints to produce positive signals. Alternative to such strain gauges mechanical deflections or electrical switches could be used to suitable advantage.

The addition of a second signal in the operational logic allows the exclusion of some common force vector stimuli that are able to energise one or the other signal on their own, but not both together. This permits to narrow the range of force vectors 101 as illustrated in FIG. 1 that can energise the opening of a valve to the extent that, within normal use patterns (such as walking, walking down stairs, walking down slope, sudden stopping, tripping, wading through water and long grass, etc.), this only happens under voluntary control, and to the exclusion of inadvertent collapse. Reference is again made to Kaufman et al. with respect to the particular normal abnormal uses of an artificial leg, and the failures noted in different knee designs.

Whereas in the embodiment in FIG. 10 the AND gate (the parting of valve member 1001 and 1002) and the memory function 1102 (the distance of the parted members 1001 and 1002 being maintained by the flow through the open valve) are combined in one, an electrical evaluation of the same mechanical inputs is a less preferred alternative due to the fact that batteries are required or an onboard electricity generator, that all needlessly add to complexity.

The present invention thus provides an AND gate functionality, which provides a LOGICAL evaluation instead of an ON/OFF evaluation, and provides new logic in this field of medical devices whereby safety is ensured independently of patient experience/skill/ability.

Figure 12:
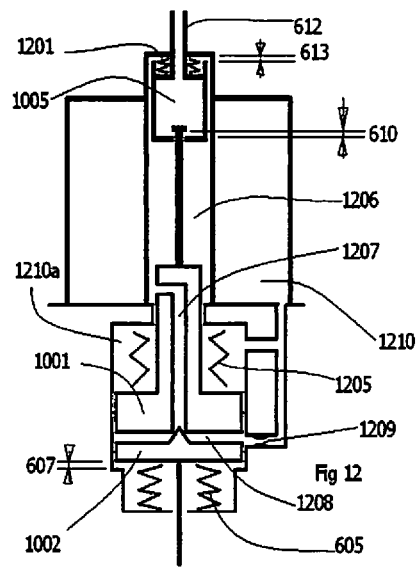
FIG. 12 shows a further detail of the controlling valve and memory.

For further clarification of the workings of the AND gate, FIG. 12 shows piston 612 that, on extension of the joint i.e. being pulled upwards, compresses resilient member 1201 to cause a delimited displacement 613 which on maximum level has a signal strength=1. This will be less than distance 610, so that a zero gap 613 (signal strength=1) is insufficient to part valve bodies 1001 and 1002.

It also shows resilient member 605 (be it in a different location as in FIG. 10) that will permit a delimited displacement 607. When distance 607 is a zero gap its signal strength is 1 such that this displacement is insufficient to cause gap 610 to close fully. Indeed both signals 613 and 607 are required to cause gap 610 to come to zero so that valve bodies 1001 and 1002 MUST part despite the effort of biasing valve-closing element 1205. This is the AND-GATE: the requirement of both signal 613 and 607 to occur for valve bodies 1002 and 1002 to part.

Once piston 612 depresses the fluid in space 1206 through passage 1207 into valve space 1208 (when the bodies 1001 and 1002 are parted) meeting a resistance in 1209 and flowing to accumulator space 1210. A pressure difference dP between those pressures in valve spaces 1208 and 1210a keeps valve body 1001 lifted against the force of valve closing biasing element 1205. This forms a memory effect. When piston 612 extends again, the said pressure differential dP disappears and valve body 1001 is depressed by biasing element 1205 onto body 1002. Other flow paths are not shown.

The invention claimed is:

1. A hydraulic non-microprocessor controlled prosthetic knee joint assembly (600) comprising:
    an upper element (601) hinged with respect to a lower element (603, 605, 608) about a knee axis (602);
    the lower element comprising a main elongate member (603) with a resilient region (605, 608) operable to provide a range of movement (610) with respect to the main elongate member (603) about an auxiliary axis (604) distal to the knee axis; and
    a hydraulic damper (614) pivotally attached to said upper element (601) and to said main elongate member (603), said hydraulic damper being operable to provide damping in a first, high level of damping and a second, low level of damping about the knee joint axis (602) and to control hinge movement of the knee joint assembly;
    wherein the knee joint assembly upon an action of hyperextension about the knee joint axis (602) is operable to act as a first sensor to provide a first displacement signal (613);
    wherein the knee joint assembly upon an action of hyperextension about said auxiliary axis is operable to act as a second sensor to provide a second displacement signal (607);
    wherein the hydraulic damper, in use and upon first and second displacement signals both exceeding a threshold condition is operable to cause a change of state of damping resistance to knee flexion about the knee joint axis from a high level to a low level;
    whereby to permit the upper element to initiate said knee flexion for a swing phase of gait, and to permit the low level of resistance to knee flexion to be sustained during continued flexion; and
    whereupon the high level of resistance to knee flexion about the knee joint axis is reinstated upon extension of the knee, said high level of resistance being maintained in the event that:
        the flexed knee joint, which represents a below threshold first displacement signal, hyperextends about said auxiliary axis, which represents an above threshold second displacement signal; or,
        the extended knee joint, which represents an above threshold first displacement signal, flexes about said auxiliary axis, which represents a below threshold second displacement signal.

2. A hydraulic non-microprocessor controlled prosthetic knee joint assembly according to claim 1, wherein the first sensor is comprised of a mechanical flexion sensor.

3. A hydraulic non-microprocessor-controlled prosthetic knee joint assembly according to claim 1, wherein the first sensor is comprised of a of a pressure sensor.

4. A hydraulic non-microprocessor controlled prosthetic knee joint assembly according to claim 1, wherein the first sensor is comprised of a strain sensor.

5. A hydraulic non-microprocessor controlled prosthetic knee joint assembly according to claim 1, wherein the first sensor is comprised of a posterior-anterior strain comparator element.

6. A hydraulic non-microprocessor controlled prosthetic joint assembly according to claim 1, wherein the second sensor is comprised of a mechanical flexion sensor.

7. A hydraulic non-microprocessor controlled prosthetic knee joint assembly according to claim 1, wherein the second sensor is comprised of a posterior-anterior strain comparator element.

8. A hydraulic non-microprocessor controlled prosthetic knee joint assembly according to claim 1, wherein the hydraulic damper element is operable in each of the following states of movement about the joint axis under conditions of flexing or extending, upon bending a distal end of the lower element toward the upper element or upon extending a distal end of the lower element away from the upper element, respectively:
   a. first state of movement—operable to return a relatively high resistance to a joint-flexing effort;
   b. second state of movement—operable to return an initial relatively low resistance to a joint-flexing effort that is sustained by the damper on continued knee flexion, and this sustained low resistance is disabled on entering the
   c. third state of movement—operable to return a relatively low resistance to a joint-extending effort,
   wherein said high resistance to a joint-flexing effort are measured relative one to another
   wherein the knee joint assembly axis of pivotal motion has a first range of motion about which the joint is in a state of flexion, and a second but smaller range of motion, with a direction dependent upon a force acting on the distal end of the lower element of the knee joint assembly at any given time, said force arising from contact with a surface, when in use;
   wherein the knee joint assembly further has a second auxiliary axis of limited pivotal flexural movement and pivotal extending movement as determined by the resilient region (605, 608);
   wherein a state of deflection of the resilient region (605, 608) generates a second positive signal; and
   wherein the knee joint assembly further includes a means to activate the second state upon determination of both the first and second signals satisfying a predetermined condition for switching.

9. A hydraulic non-microprocessor controlled prosthetic knee joint according to claim 8, wherein the second auxiliary axis is approximated by a structural resilient member.

10. A hydraulic non-microprocessor controlled prosthetic joint according to claim 8, wherein the second auxiliary axis is approximated by a structural resilient member and wherein the structural resilient member also performs the function of the second resilient member.

11. A hydraulic non-microprocessor controlled prosthetic knee joint assembly according to claim 1, wherein the first resilient member is a resilient external body of the joint.

12. A hydraulic non-microprocessor controlled prosthetic knee joint assembly according to claim 1, wherein said knee joint assembly further has an effective second auxiliary axis of limited pivotal flexural movement and pivotal extending movement (604) as determined by the resilient region (605, 608) of the lower element (603).

13. A hydraulic non-microprocessor controlled prosthetic knee joint assembly according to claim 1, wherein said knee joint assembly further has a physical second auxiliary axis of limited pivotal flexural movement and pivotal extending movement (604) as determined by the lower element (603).

14. A hydraulic non-microprocessor controlled prosthetic knee joint assembly comprising an upper element hinged with respect to a lower element (603) about a knee joint axis (602); the lower element (603) comprising a main elongate member with a resilient region (605, 608) situated distal to the knee joint axis and operable to provide a range of movement (610) about an auxiliary axis (604) distal to the knee axis; and a hydraulic damper operable to provide damping in each of first and second states of movement about the knee joint axis, said hydraulic damper also being operable to control hinge movement, in one of first and second states of resistance;
   wherein the knee joint assembly upon an action of hyperextension about the knee joint axis (602) is operable to provide a first displacement signal (613); and,
   wherein the knee joint assembly upon an action of hyperextension about said auxiliary axis is operable to provide a second displacement signal (607);
   wherein the hydraulic damper, upon first and second displacement signals both being positive, is permitted to change state from a high level of damping to a low level of damping
   wherein the first displacement signal arises upon a moment of hyperextension due to a force vector passing anterior to the knee joint axis, said force vector arising from contact with a surface, when in use, and wherein the second displacement signal arises upon another hyperextension moment due to the same force vector passing anterior to the auxiliary axis;
   wherein upon first and second signals both being positive to their respective required values, the hydraulic damper is permitted to change state;
   wherein said knee joint assembly is operable under the following states of operation:
      a. first state of operation—operable to return a high resistive torque to a joint-flexing effort;
      b. second state of operation—operable to return a low resistive torque to a joint-flexing effort;
      c. third state of operation—operable to return a low resistive torque to a joint-extending effort,
   wherein said knee joint assembly has a principal axis of pivotal motion with a first range of motion about which the knee joint assembly is in a state of flexion, and said principal axis also permits a second but small range of motion that is operational in accordance to direction and location of force vectors passing about it arising from contact with a surface, when in use;
   wherein said knee joint assembly further has a second auxiliary axis of limited pivotal flexural movement and pivotal extending movement as determined by the resilient region (605, 608);
   wherein the state of deflection of the said resilient region (605, 608) represents a second positive signal; and
   wherein the said knee joint assembly further comprises a means to activate the second state upon determination of both the first and second signals satisfying a predetermined condition for switching.

15. A hydraulic non-microprocessor controlled prosthetic knee joint assembly according to claim 14, wherein the second auxiliary axis is provided by the resilient region (605, 608).

16. A hydraulic non-microprocessor controlled prosthetic knee joint assembly according to claim 14, wherein the resilient region (605, 608) comprises a second resilient member.

17. A hydraulic non-microprocessor controlled prosthetic knee joint according to claim 14, wherein the first resilient member is a resilient external body of the knee joint assembly.

18. A hydraulic non-microprocessor controlled prosthetic knee joint assembly according to claim 14, wherein the lower element (603) has a resilient element comprising a resilient region of the main elongate member.

* * * * *